United States Patent [19]

Hasson

[11] 4,174,715
[45] Nov. 20, 1979

[54] MULTI-PRONGED LAPAROSCOPY FORCEPS

[76] Inventor: Harrith M. Hasson, 345 Fullerton Pkwy., Chicago, Ill. 60614

[21] Appl. No.: 781,678

[22] Filed: Mar. 28, 1977

[51] Int. Cl.² ............................................. A61B 17/28
[52] U.S. Cl. .................. 128/321; 128/303.14
[58] Field of Search .................. 128/303 A, 4, 321, 3, 128/303.15, 303.13, 303.14

[56] References Cited

U.S. PATENT DOCUMENTS

| | | | |
|---|---|---|---|
| 2,137,710 | 11/1938 | Anderson | 128/321 |
| 2,670,519 | 3/1954 | Recklitis | 128/321 X |
| 3,989,049 | 11/1976 | Yoon | 128/303 A X |
| 4,043,323 | 8/1977 | Komiya | 128/4 |
| 4,103,680 | 8/1978 | Yoon | 128/303 A X |

*Primary Examiner*—Robert W. Michell
*Assistant Examiner*—Michael H. Thaler
*Attorney, Agent, or Firm*—Norman Lettvin

[57] ABSTRACT

Multi-pronged spring-loaded laparoscopy instruments are provided for use in tubal sterilization, ovarian mobilization and biopsy. The instruments include three or four expandable prongs for holding tissue in a stable position. The instrument may be provided with a plug for access to an inner biopsy channel or central bore for facilitating ovarian biopsy. A slotted bushing may be provided with offset apertures to enable the surgeon to hold the prongs in preselected positions without exerting pressure on the handle of the instrument. When desired, the instrument may be provided with a manually remote-controlled cutting edge at the forward tip of the instrument to resect a segment of the coagulated tube during tubal sterilization.

11 Claims, 13 Drawing Figures

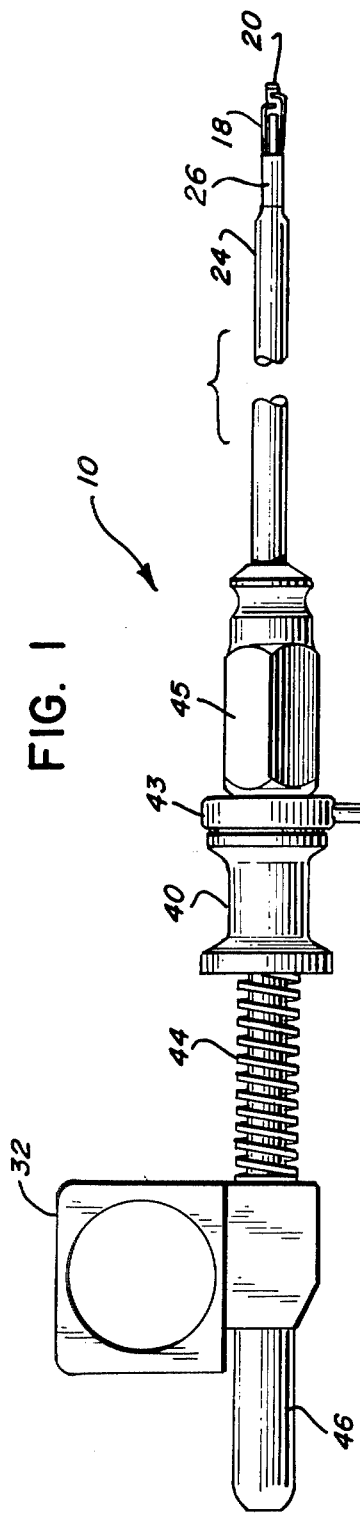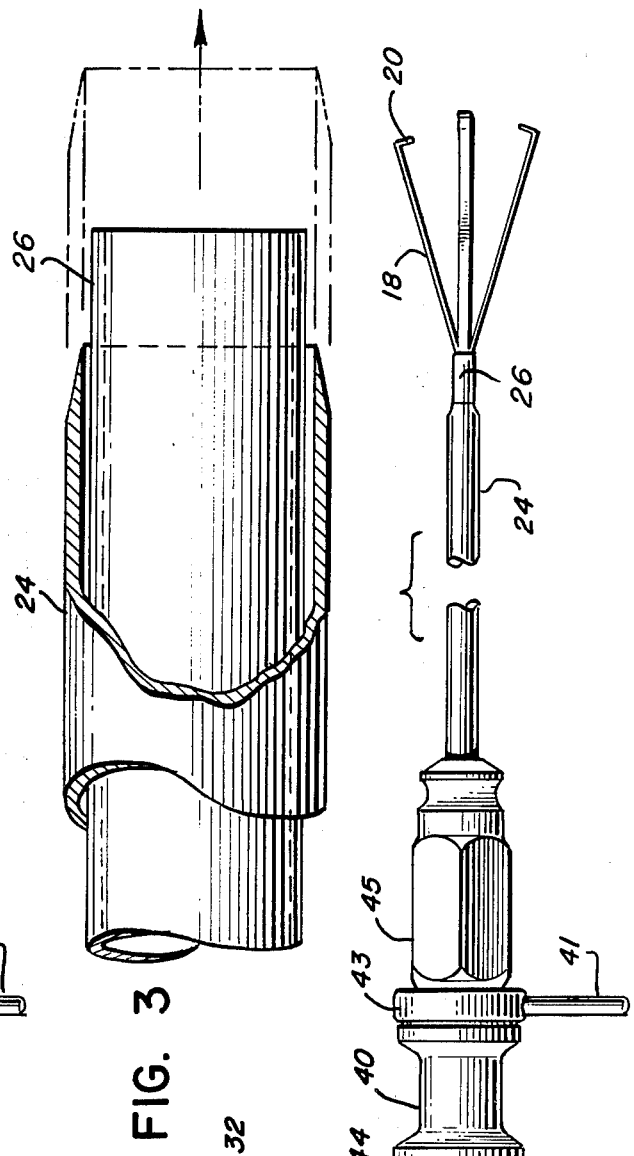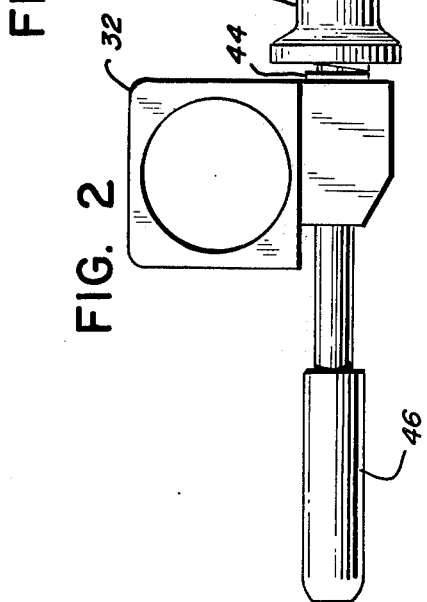

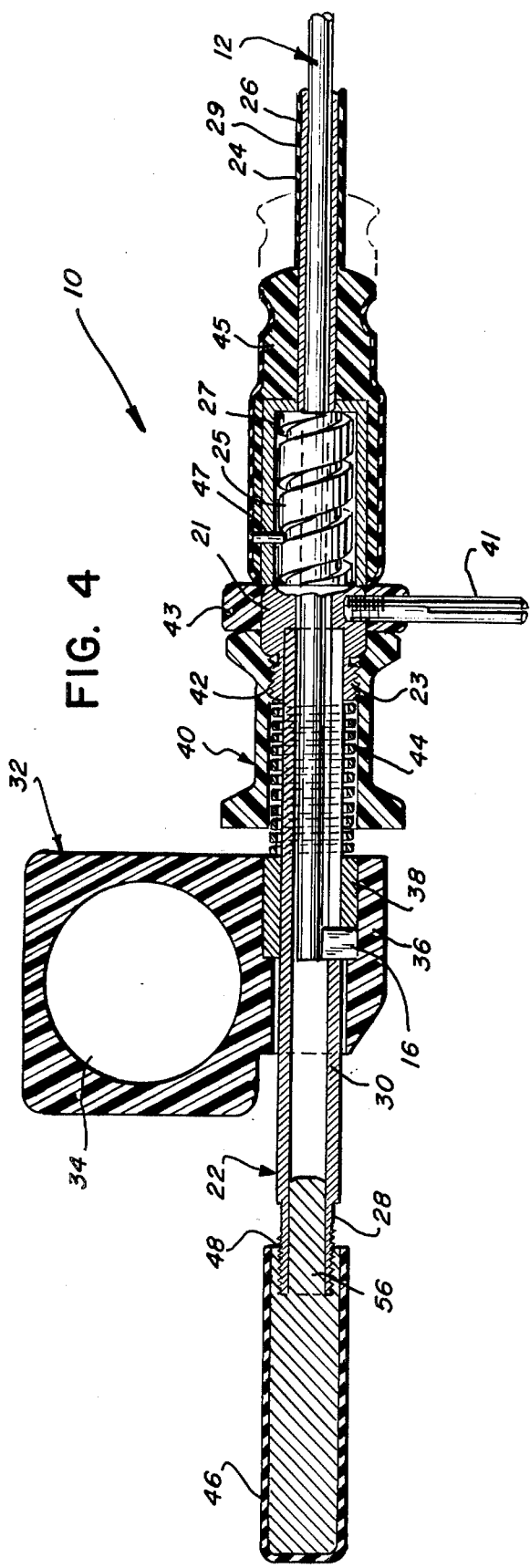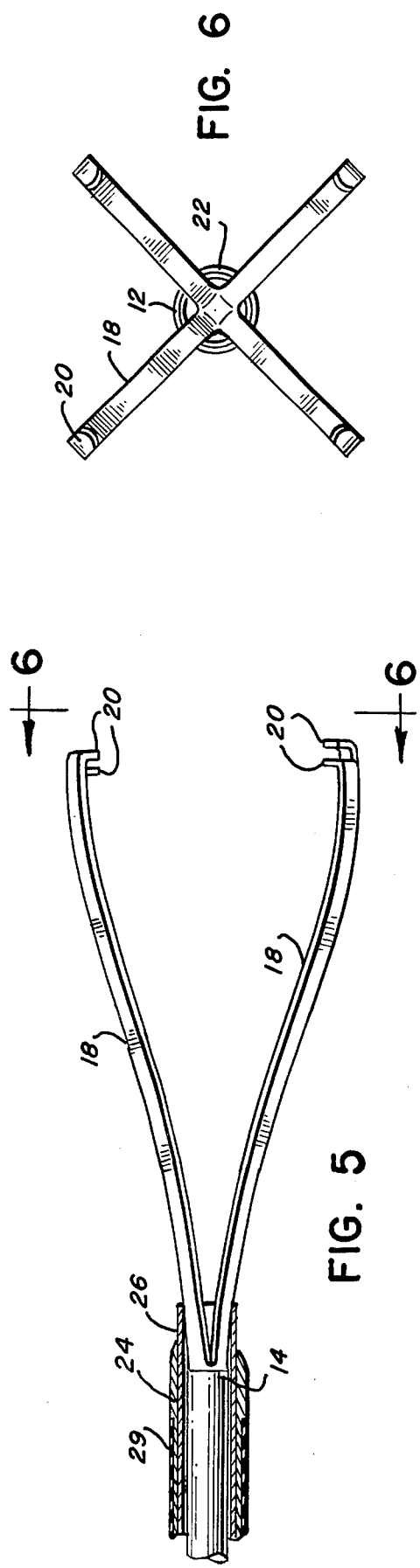

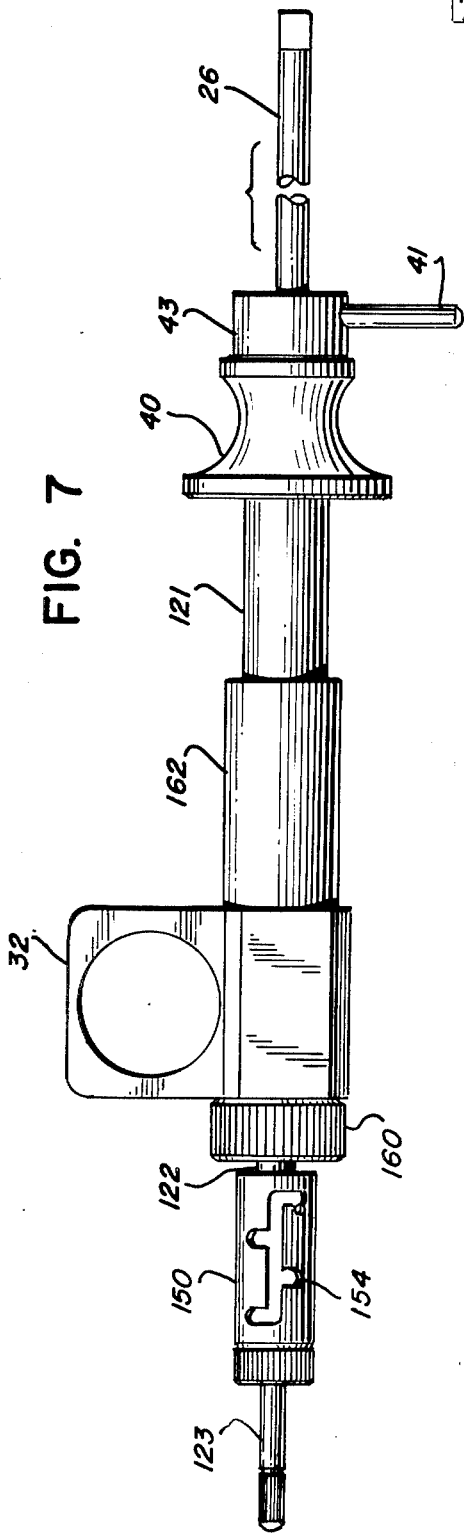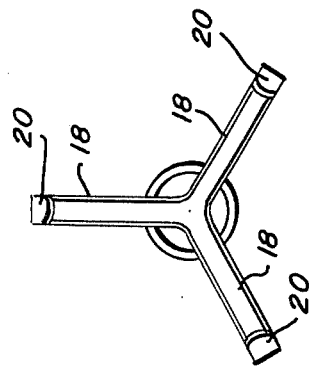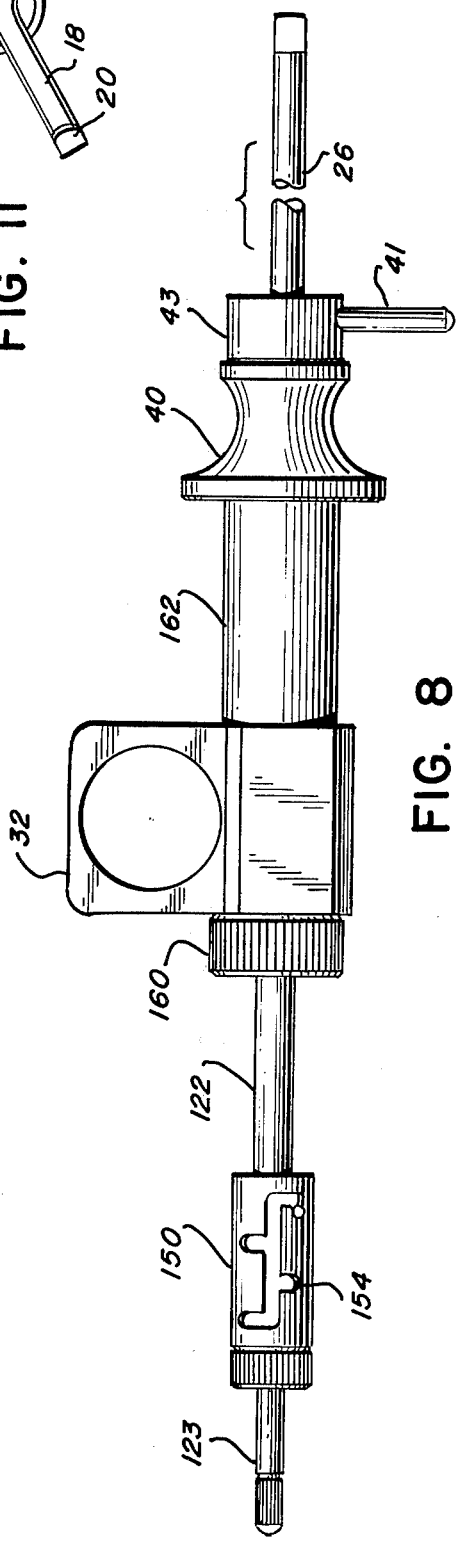

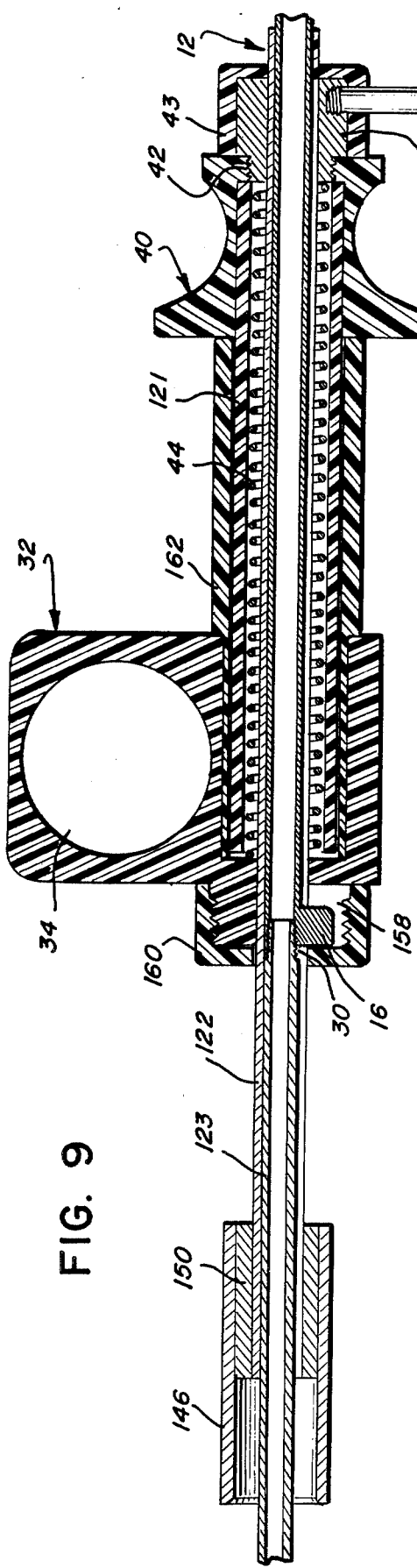
FIG. 9
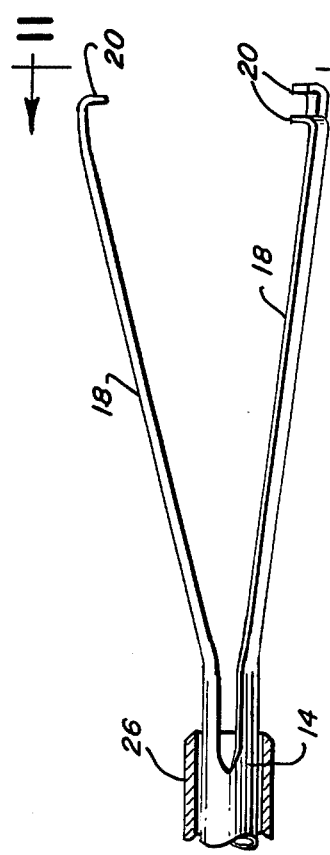
FIG. 10
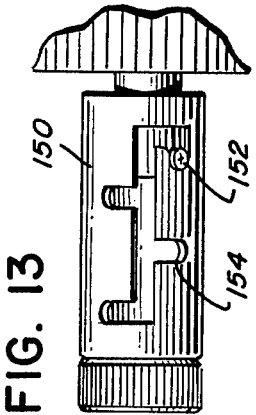
FIG. 13
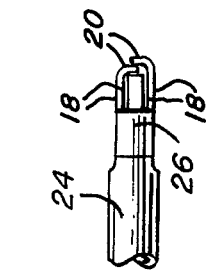
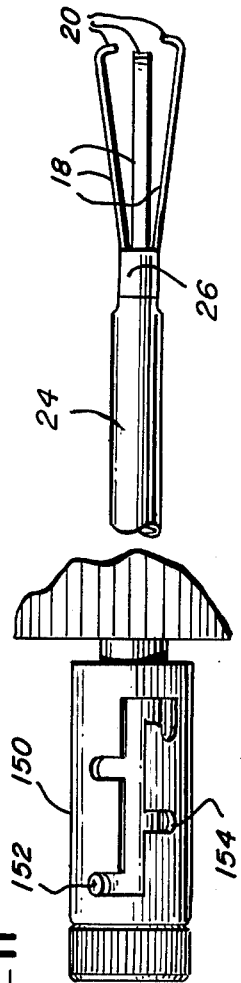
FIG. 12

MULTI-PRONGED LAPAROSCOPY FORCEPS

BACKGROUND OF THE INVENTION

This invention relates to a forceps, and more particularly, to multi-pronged forceps for use in laparoscopy.

Use of conventional two-pronged forceps in laparoscopic surgery pose problems. Fallopian tubes held by these instruments tend to slip. It is also difficult to grasp ovaries securely by existing forceps. Furthermore, when removing the forceps to collect a biopsy specimen prior to cauterization of the site, the ovary must be released and it is then difficult to regain prompt control of the ovary, especially when there is bleeding which tends to obscure the operative field and which makes more difficult the holding with the forceps of the ovary for purpose of cauterization. Biopsy forceps of the alligator type, having hinged jaws with limited opening, continue to display similar deficiencies.

SUMMARY OF THE INVENTION

One object of this invention is to provide improved forceps which holds tissue securely under substantially even tension, which require minimum effort to maintain tissue in held condition, and which have self-holding character.

In accordance with principles of the present invention, there is provided forceps for preferred, but not exclusive, use in laparoscopic surgery such as tubal sterilization, ovarian mobilization, biopsy and the like. The forceps includes at least three elongated flexible prongs adapted to be moved between an open, or spread apart, position and a closed position for grasping tissue. Each of the elongated prongs has at its outermost end, or tip, a blunt finger that projects radially inwardly and being constructed and arranged to avoid puncturing the tissue, so as to decrease the likelihood of trauma during laparoscopic surgery. The elongated prongs are preferably each of a slightly different length so that the inwardly extending fingers may be positioned longitudinally adjacent each other, and with the lengths of the prongs clustered into a minimal circumferential area, as when the prongs have been moved toward their closed position, for purposes of minimizing the cross-sectional size of the instrument when inserting the forceps through a surgical access incision.

In the illustrated embodiment, the preferred instrument includes an internal elongated shaft coupled to the prongs, and an outer elongated tubular sleeve for slidably receiving the internal shaft and portions of the flexible prongs. The internal shaft is longitudinally movable between an extended position, in which the forceps prongs project outwardly of the forwardmost tip of the outer sleeve, and a fully retracted position in which the prongs are clustered together or closed and for the most part confined within the outer sleeve, but with the fingers of the prongs still extending forwardly of the forwardmost tip of the sleeve. The instrument further includes spring means for normally urging the internal shaft toward the retracted position.

A more detailed explanation of the invention is provided in the following description and appended claims taken in conjunction with the accompanying drawings.

BRIEF DESCRIPTION OF THE DRAWINGS

FIG. 1 is a side elevational, fragmentary, view of an instrument, provided with a four-pronged forceps portion that is shown in a retracted position, constructed in accordance with the present invention;

FIG. 2 is a view similar to FIG. 1 but showing the forceps portion of the instrument in a forwardly extended position with the prongs of the forceps spread apart;

FIG. 3 is an enlarged, fragmentary break-away view, partly in elevation and partly in cross-section, showing portions of the sleeve and slidable internal shaft of the instrument of FIGS. 1 and 2;

FIG. 4 is an enlarged cross-sectional and break-away view of a portion of the instrument shown in FIGS. 1 and 2;

FIG. 5 is an enlarged fragmentary view, showing the elongated forceps of the instrument of FIGS. 1 and 2, and partially illustrating the different lengths of the prongs;

FIG. 6 is an end view of the forceps shown in FIG. 5, and is taken substantially along line 6—6 shown in FIG. 5;

FIG. 7 is a fragmentary side elevational view similar to a portion of FIG. 1, showing an instrument for use with a three-pronged forceps, and showing parts of the instrument in a position in which the forceps prongs are projected forwardly;

FIG. 8 is a view similar to FIG. 7 but showing portions of the instrument at a position in which the forceps prongs are retracted;

FIG 9 is a view similar to the cross-sectional view of FIG. 4, but showing portions of the instrument of FIGS. 7 and 8;

FIG. 10 is a view similar to FIG. 5 but showing the three-pronged forceps of the instrument of FIG. 7 in forwardly projected position with the forceps prongs spread apart;

FIG. 11 is an end view of the three-pronged forceps shown in FIG. 10, and is taken substantially at the line 11—11 shown in FIG. 10;

FIG. 12 is a fragmentary view of portions of the instrument of FIGS. 7-11 showing the forceps prongs held at a position intermediate between being fully projected and fully retracted;

FIG. 13 is a view similar to FIG. 12 but showing the forceps prongs of the instrument in their fully retracted position.

DETAILED DESCRIPTION OF THE ILLUSTRATIVE EMBODIMENT

Referring first to the FIGS. 1-6 embodiment of the laparoscopy instrument generally depicted as 10 in the drawings, an elongated stem 12 is received within an elongated tubular guide means 22 having finger grip means 40. A thumb-operated actuator 32 is operatively connected to the stem and biased by spring means 44 to normally urge the stem rearwardly to project a plurality of elongated forceps arms 18 inwardly to a clustered, closest together position.

The stem 12 is an elongated tubular rod having a forward forceps arms receiving end 14 and a rearward end formed with a short, transversely extending tongue 16. A plurality of stainless steel forceps arms 18 extend from the forceps arms receiving end of the stem 12. The number of arms may vary but three or four have been found to be best suited for the surgical procedures described herein. Each arm 18 is of a different length as best seen in FIGS. 10 and 12-13 and has an inturned finger 20 at its distal end. The ends of the fingers are blunt to avoid puncturing the tissue which decreases the likelihood of trauma during laparascopic surgery. By so constructing the forceps arms, they may be clustered close together with each finger 20 lying adjacent at least one other finger but without contacting any other finger, as seen in FIG. 13. The forceps arms 18 are so mounted or formed on stem 12 as to be normally, resiliently biased outwardly, away from each other. When the arms are cammed toward each other, the fingers move radially toward the trace of a line through two other inturned fingers to thus provide greater tissue gripping function.

Surrounding the elongated stem 12 is a stainless steel, elongated, tubular guide means 22 which is externally coated with a plastic or rubber insulating material. The forward end portion 24 of the tubular guide means 22 includes a tubular sleeve 26 which is maintained at all times forwardly of the forward prong end 14 of the elongated stem 12. The elongated stem is slidable within the tubular guide means such that the forceps arms 18 may be cammed by the tubular sleeve 26 to draw their distal ends toward a clustered relationship when the stem is moved rearwardly. Surrounding the forward end of the tubular sleeve 26 is an outer tube 29 coated with an insulating material such as Delrin. The forward end of sleeve 26 normally extends beyond tube 29 which tube 29 has its forwardmost circular edge sharpened razor-sharp to provide a circular knife. The rearward end of the tubular guide means 22 is both threaded as at 28 and includes a longitudinally extending, thumb-operated actuator connecting slot 30. The transverse stem tongue 16 extends through the actuator connecting slot 30.

Connecting the rear portion of the tubular guide means 22 with the forward tubular sleeve 26 is a guide connection ring 21 having an externally threaded rearward side 23. Soldered to the forward side of the guide ring 21 is an elongated guide sleeve 25 including a spiral stud receiving groove 27.

A thumb-operated actuator 32 includes an aperture or ring 34 for receiving a surgeon's thumb. The thumb actuator 32 is generally rectangular in cross-section and includes a depending tubular sleeve 36 which surrounds the tubular guide means 22. The tubular sleeve is counterbored at its forward end to seat the stem tongue 16 therein while an elongated ring 38 fills the remainder of the bore.

Positioned forward of the thumb-operated actuator 32 and also surrounding the tubular guide means 22 is a tubular finger grip means 40 having a concave external surface for receiving the index and middle fingers of an operating surgeon. The forward portion of the finger grip means 40 is internally threaded at 42 for stationary connection to the guide connection ring 21 of the tubular guide means 22. The remainder of the internal portion of the finger grip means is recessed.

A coiled compression spring 44 is of a diameter to closely surround the tubular guide means 22. One end of the spring rests in the finger grip means recess against the threaded side 23 of the guide ring 21, while the other end abuts the ring 38 in the thumb actuator counterbore. The uncompressed length of the spring 44 is such as to apply a force on the thumb actuator even if it slides to the rearward end of the tubular guide means.

When desired, an electric cautery device 41 may be attached to the guide connection ring 21. A cautery device receiving bushing 43 is positioned over the ring 21 to abut the forward end of the finger grip means 40.

The ring 21 and bushing 43 are appropriately tapped to threadedly receive the cautery device 41.

A manually rotatable collar 45 slidably surrounds the tubular guide means 22. The rearward end of the rotatable collar 45 includes a large diameter recess to encapsulate the spiralled guide sleeve 25. A radially inward projecting stud 47 extends from the rearward end of the rotatable collar 45 and rides in the spiral groove 27. The forward end of the rotatable collar 45 is connected to the rearward end of the outer tube 29 such that the tube 29 is reciprocably slidable in response to rotation of the collar 45.

The rearward end of the tubular guide means 22 has threaded thereto an elongated abutment sleeve 46. The abutment sleeve 46 is fabricated from metal and has a forward edge 48 adapted to be contacted by the thumb-operated actuator which is spring biased thereagainst. A stainless steel plug 56 may be placed within the tubular guide means 22 to provide a removable closure for the elongated inner biopsy channel defined by said tubular guide means.

Referring now to the three pronged instrument of FIGS. 7-13, three forceps arms 18 are shown extending forwardly from the elongated stem 12. While the four prong laparoscopy forceps has four arms spaced at right angles to each other, the three pronged instrument has three arms spaced at about 120 degree intervals. The lengths of the arms still differ slightly so that those fingers may also be clustered close together without contacting each other.

The embodiment of FIG. 9 shows a variation of the FIGS. 1-6 embodiment. The tubular stem 12 is identical with that of FIG. 4 except that its rearward end is internally threaded. Slidably surrounding the stem is a modified guide means comprising an elongated tube 122 having a longitudinal thumb-actuator connecting slot 30 proximate its rearward end. The threaded rear portion of the stem 12 is connected to an externally threaded extension shaft 123.

An internally threaded bushing 150 is attached to the rearward end of the tubular guide means 122 and includes a radially outward extending lug 152. An elongated abutment sleeve 146 is slidably received over bushing 150 and is slotted to provide a plurality of offset detents 154 for receiving the control lug 152.

The thumb-operated actuator 32 has a tubular rearward extension 158 which is externally threaded for fixed engagement with an internally threaded, externally knurled Delrin cap 160. The tubular finger grip means 40 and the guide ring 21 are substantially identical with the FIG. 4 embodiments and again a coiled compression spring 44 of a diameter to surround the tubular guide means 122 rests at one end against the guide ring 21 and at the other end abuts the recess in the thumb-operated actuator 32.

The guide means 122 further includes a second concentric elongated tube 121 surrounding the coiled compression spring 44 and extending longitudinally between the recesses in the thumb-operated actuator 32 and the finger grip means 40. The thumb-operated actuator 32 is connected to a forwardly extending outermost sleeve 162 that is positioned to telescope over the outer elongated tube 121.

OPERATION

The operation of the three-prong and four-prong laparoscopy forceps are similar to each other. In each case the instrument is held by the thumb-operated actuator and the finger grip means. Movement of the thumb-operated actuator towards the finger grip means causes the stem to move forward so that the prongs project to an open or expanded position forwardly of the tubular guide tube. Such movement causes the coil spring to compress and moves the outermost sleeve from a rearward position as shown in FIG. 7 to a forward position abutting the finger grip means as shown in FIGS. 8 and 9. When manual pressure exerted against the thumb-operated actuator is released, the spring returns to its natural, uncompressed, state causing the stem to move rearwardly until the prongs are cammed inwardly to the fully retracted position as shown in FIGS. 1 and 13.

Although only the FIGS. 7-13 embodiment is shown equipped with a slotted abutment sleeve, it is to be understood that the embodiment of FIGS. 1-6 could also be so equipped. When the forceps are supplied with the abutment sleeve, the sleeve may be rotated so that the control lug engages one of the offset detents to lock the prongs in a stationary position. The offset detents of the slotted sleeve are so spaced that the surgeon may select four stationary positions of the prongs ranging from partially open to fully closed without maintaining pressure on the thumb-operated actuator of the handle.

The four-pronged laparoscopy forceps may also be used as a surgical cutting blade. The forwardmost circular edge of outer tube 29 being razor sharpened may be extended or retracted along tubular sleeve 26 by rotating collar 45. As the collar rotates, the stud 47 follows the spiral groove in guide sleeve 25 to translate the collar and the outer tube on the tubular sleeve. When the collar is rotated to its forwardmost position, the sharpened circular edge extends beyond the prongs.

The multi-pronged laparoscopy forceps may be used for ovarian mobilization, biopsy, and tubal sterilization by means of coagulation and resection. For tubal sterilization, the four-pronged laparoscopy forceps may be introduced into the abdominal cavity through a second puncture sleeve whereupon the prongs may be opened and positioned around the fallopian tube approximately 1.5 centimeters from the uterus. The prongs may then be retracted to hold the tube securely. Care should be exercised to grasp the tube with a minimal amount of adjoining mesosalpinx to prevent the occurrence of bleeding. A fiberglass sleeve may be advanced over the forceps which can be withdrawn in order to place the fallopian tube inside the sleeve. Care should also be exercised to avoid excessive tension on the tube. A cord to the electric cautery unit can be connected to the forceps and current passed therethrough in repeated bursts of three-to-five seconds until adequate coagulation is obtained. The rotating knife can be brought down to resect a segment of the coagulated tubes held by the forceps. The instrument can then be withdrawn with the resected segment and the process repeated on the other side.

Ovarian mobilization can be carried out by either the three-or-four prong forceps. The prongs should be opened to grasp the ovary by its convex-free margin, away from the hilum. The ovary can be held under tension by means of the retracted prongs and manipulated as needed. Following complete inspection, the prongs may be expanded slightly to release the ovary.

Ovarian biopsy can be performed with the three-prong forceps. The ovary can be held and grasped under tension as previously described. The surgeon may then introduce a small biopsy instrument through the inner channel or central bore of the inner shaft to obtain a specimen. The biopsy instrument can then be removed and a probe with an active cautery tip can be introduced through the channel or bore to coagulate bleeding areas.

The spring-loaded laparoscopy instrument described herein offers certain advantages. Such an instrument holds tissue securely with even tension and only a minimal effort is necessary to maintain the held tissue in a stable position. The prongs are advantageously constructed and arranged so that when they are normally closed they occupy minimal circumferential area to minimize the surgical access incision. One unique feature of the three-prong laparoscopy instrument is that it allows ovarian biopsy and subsequent cauterization to be undertaken under conditions of uninterrupted control. For small flattened ovaries, biopsy is best accomplished by small alligator forceps directed through a third puncture.

Although an embodiment of the invention has been shown and described, it is to be understood that various modifications and substitutions may be made by those skilled in the art without departing from the novel spirit and scope of the invention.

What is claimed is:

1. An improved forceps for use with a laparoscopy instrument of the type that includes elongated tubular guide means having a forward end, finger grip means secured to said guide means distally from said forward end, elongated stem means having a portion thereof slidable in said tubular guide means, and a thumb-operated actuator connected to said stem means for selectively moving said stem means longitudinally along said tubular guide means responsive to movement of the thumb-operated actuator toward and away from the finger grip means;

said improved forceps including a tubular sleeve as the forward portion of said tubular guide means, the elongated stem having a forward prong end arranged to move within the tubular sleeve toward and away from the forward end of said sleeve but with said forward prong end always positioned rearwardly of the forward end of the tubular sleeve, at least three elongated flexible forcep arms of resilient steel each having a base end thereof secured to the forward prong end of the elongated stem so that a portion of each forceps arm is at all times telescoped within the forwardmost portion of the tubular sleeve, each forcep arm being of a different length and having an inturned finger at the distal end thereof constructed and arranged so that when said fingers at the distal ends of the forcep arms are clustered closest together each finger lies adjacent and overlapping adjacent fingers but does not contact any other finger, said fingers when clustered closest together and overlapping being spaced forwardly of the forward end of the tubular sleeve, each forcep arm being biased to normally spring outwardly away from the other forcep arms when the elongated stem is projected forwardly, but being cammed by the extended end of the tubular sleeve to draw the distal ends of the forcep arms toward a clustered relationship when the elongated stem is moved rearwardly, and spring means operative associated with the finger grip means and thumb-operated actuator for normally biasing said elements apart and to tend to move the elongated stem rearwardly, the finger grip means on the rearward side thereof being recessed, and said spring means being an elongated coil spring one end of which enters the recessed rearward side of the finger grip means.

2. Forceps as in claim 1 wherein each inturned finger is constructed, and arranged relative to the other fingers so that, when the forcep arms are cammed toward each other, the finger moves radially toward the trace of a line through two other inturned fingers, to thus provide for greater tissue gripping function by the forceps.

3. Forceps as in claim 1 wherein the elongated stem is a tubular member.

4. Forceps as in claim 1 wherein the fingers at the ends of the forcep arms are blunted, so as to be atraumatic, and being of a radial length less than the inner diameter of the tubular sleeve.

5. Forceps as in claim 1 wherein the tubular guide means includes a longitudinally slotted sleeve, the stem having a tongue located rearwardly of the finger grip means and extending radially outwardly through the slot in the tubular guide means, and the tongue being operatively connected to said thumb-operated actuator.

6. Forceps as in claim 1 including spacing means for selectively latching the thumb-operated actuator at a plurality of selected axial spacings from the finger grip means.

7. Forceps as in claim 6 wherein the spacing means includes a projection that is fixed relative to the finger grip means and is located rearwardly to the thumb-operated actuator, an elongated abutment sleeve located rearwardly of the thumb-operated actuator and having a forward end positioned to be engaged by the actuator which is spring biased rearwardly;

and means on said abutment sleeve arranged to cooperate with said projection to selectively locate the forward end of the abutment sleeve at different spacings forwardly of said projection.

8. Forceps as in claim 1 wherein the tubular guide means includes an elongated tubular rear part that is colinearly aligned with the tubular sleeve.

9. Forceps as in claim 8 including a selectively removable plug secured to the rearward end of the tubular rear part of the tubular guide means, for selectively providing or denying access through the tubular stem.

10. An improved forceps for use with a laparoscopy instrument of the type that includes elongated tubular guide means having a forward end, finger grip means secured to said guide means distally from said forward end, elongated stem means having a portion thereof slidable in said tubular guide means, and a thumb-operated actuator connected to said stem means for selectively moving said stem means longitudinally along said tubular guide means responsive to movement of the thumb-operated actuator toward and away from the finger grip means;

said improved forceps including a tubular sleeve as the forward portion of said tubular guide means, the elongated stem having a forward prong end arranged to move within the tubular sleeve toward and away from the forward end of said sleeve but with said forward prong end always positioned rearwardly of the forward end of the tubular sleeve, at least three elongated flexible forcep arms of resilient steel each having a base end thereof secured to the forward prong end of the elongated stem so that a portion of each forceps arm is at all times telescoped within the forwardmost portion of the tubular sleeve, each forcep arm being of a different length and having an inturned finger at the distal end thereof constructed and arranged so that when said fingers at the distal ends of the forcep arms are clustered closest together each finger lies adjacent and overlapping adjacent fingers but does not contact any other finger, said fingers when clustered closest together and overlapping being spaced forwardly of the forward end of the tubular sleeve, each forcep arm being biased to normally spring outwardly away from the other forcep arms when the elongated stem is projected forwardly, but being cammed by the extended end of the tubular sleeve to draw the distal ends of the forcep arms toward a clustered relationship when the elongated stem is moved rearwardly, and spring means operative associated with the finger grip means and thumb-operated actuator for normally biasing said elements apart and to tend to move the elongated stem rearwardly, the tubular guide means including a pair of concentric members that define an annular recess therebetween, and said spring means being an elongated coil spring that is positioned in the annular recess defined between the pair of concentric members.

11. Forceps as in claim 10 wherein the thumb-operated actuator connects to a forwardly extending sleeve that is constructed and positioned to telescope over the outer one of said pair of concentric members.

* * * * *